United States Patent [19]

Hay

[11] 4,082,808

[45] Apr. 4, 1978

[54] THIOBIS-2,6-DISUBSTITUTED PHENOL

[75] Inventor: Allan S. Hay, Schenectady, N.Y.

[73] Assignee: General Electric Company, Schenectady, N.Y.

[21] Appl. No.: 650,011

[22] Filed: Jan. 19, 1976

Related U.S. Application Data

[62] Division of Ser. No. 484,995, Jul. 1, 1974, Pat. No. 3,953,519.

[51] Int. Cl.$^2$ .............. C07C 149/36; C07C 121/20; C07C 43/20
[52] U.S. Cl. .................... 260/609 F; 260/465.8 R; 260/613 D
[58] Field of Search .................................. 260/609 F

[56] References Cited

U.S. PATENT DOCUMENTS

| | | |
|---|---|---|
| 2,629,743 | 2/1953 | Burnette et al. ............ 260/609 F |
| 3,107,233 | 10/1963 | Coffield et al. ............ 260/609 F |
| 3,377,333 | 4/1968 | Ciesielski et al. ............ 260/609 F |
| 3,494,966 | 2/1970 | Geering et al. ............ 260/609 F |
| 3,678,115 | 7/1972 | Fujisawa et al. ............ 260/609 F |

*Primary Examiner*—Lewis Gotts
*Assistant Examiner*—Molly C. Eakin
*Attorney, Agent, or Firm*—F. Wesley Turner; Joseph T. Cohen; Jerome C. Squillaro

[57] ABSTRACT

Novel thiobis-2,6-disubstituted phenols are described which are useful as monomers in the synthesis of polycarbonates, polyesters, epoxy resins, among many others chemicals synthesized from polyhydric phenols. In addition, the thiobisphenols are also useful as antioxidants.

2 Claims, No Drawings

THIOBIS-2,6-DISUBSTITUTED PHENOL

This is a division of application Ser. No. 484,995, filed July 1, 1974, now U.S. Pat. No. 3,953,519.

This invention relates to a process for the preparation of a thiobis-2,6-disubstituted phenol under reaction conditions which comprise contacting sulfur and a 2,6-disubstituted phenol in the presence of (1) a base, (2) and an anion capable of forming a conjugate acid in the presence of the phenol and the base. In a preferred embodiment, the process is carried out in the presence of catalytic amounts of an alkali metal base.

Various observations have been made by the prior art regarding reactions between phenolic reactants and sulfur carried out in the presence of a base, such as those described in:

(I) A. J. Neale's description of the preparation of monothiobisphenols and oligomeric phenols by the reaction of phenol and sulfur at temperatures of 140°–180° C. during time periods of 6 to 24 hours (*Tetrahedron*, Vol. 25, Pergamon Press (1969). Printed in Great Britain, pages 4593 to 4597);

(II) E. J. Geering's description of the preparation of a phenol-sulfide having an average of at least two sulfur atoms per linkage by the reaction of sulfur and a phenolic reactant having at least one ortho position substituted by hydrogen at temperatures of 100°–200° C. during time periods of ½ to 15 hours (A. J. Geering et al., U.S. Pat. No. 3,647,885);

(III) T. Fujisawa's description of the preparation of 4-arylthio-2,6-dialkylphenols by the reaction of 2,6-dialkylphenols and aromatic disulfides carried out at elevated temperatures during time periods of ½ to 50 hours in the presence of a solvent (Fujisawa et al., U.S. Pat. No. 3,697,601, further described by Fujisawa in the article *Sulfenylation of Hindered Phenols With Aryl Disulfides*, J. Org. Chem., Vol. 38, No. 4 (1973) pages 687–690);

(IV) T. Fujisawa, K. Hata, and T. Kojima's description of the preparation of thiobis-2,6-dialkylphenols and polythiobis-2,6-dialkylphenols by the reaction of 2,6-disubstituted sterically hindered phenols with sulfur in an alcohol at room temperatures to 100° C. during time periods of ½ to 1 hour (*Synthesis*, Vol. 1, January 1973, pages 38–39).

Other prior art publications, among others, which relate to the reaction of phenol and sulfur which illustrate the state of the art are the following:

E. J. Geering et al., U.S. Pat. Nos. 3,717,682 and 3,743,680, as well as *Rearrangements and Decompositions of Thiobisphenols* by A. J. Neale et al., Tetrahedron, Vol. 25, Pergamon Press (1969) Printed in Great Britain, pages 4593–4597.

Essentially, this invention embodies a process for the preparation of a thiobis-2,6-disubstituted phenol which comprises contacting sulfur and a 2,6-disubstituted phenol carried out in the presence of (1) a base, (2) and an anion capable of forming a conjugate acid in the presence of the phenol and the base. In a preferred embodiment, the process is carried out in the presence of catalytic amounts of base. In still another preferred embodiment, the process is carried out in the presence of a solvent. In still another preferred embodiment the process is carried out in the presence of another sulfur reaction.

The process of preparing the thiobis-2,6-disubstituted phenol of this invention comprises the reaction of any phenol having organo substituents in both of the ortho positions relative to the hydroxyl group of the phenol subject to the proviso that the substituents do not interfere with the formation of a thiobis-2,6-disubstituted phenol in accordance with the reaction parameters of this invention. Among others, phenols suited to the practice of this invention can be described by the following structural formula:

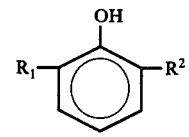

I.

wherein independently each $R^1$ and $R^2$ is a monovalent substituent selected from the group consisting of hydrocarbon and hydrocarbonoxy radicals. Preferably the hydrocarbon and hydrocarbonoxy radicals have from 1 to 30, more preferably from 1 to 15, and even more preferably from 1 to 2 carbon atoms. Further, it is still even more preferred that the hydrocarbon and hydrocarbonoxy radicals be linear radicals, i.e. free of secondary or tertiary carbon atoms along the skeletal backbone of the carbon atom chain. Representative of phenols of Formula I., among others, which can be employed are as follows:

2,6-dimethylphenol,
2,6-diethylphenol,
the 2,6-dipropylphenols (2,6-di-n-propyl and 2,6-di-sec-propylphenol),
the 2,6-dibutylphenols (2,6-di-n-butyl, 2,6-di-secbutyl, and 2,6-di-tertbutylphenol),
the 2,6-didecylphenols,
the 2,6-dietetradecylphenols,
the 2,6-dioctadecylphenols,
the 2,6-didocosylphenols,
the 2,6-dihexacosylphenols,
the 2,6-ditriacontylphenols,
2,6-diphenylphenol,
2,6-dibenzylphenol,
the 2,6-ditolylphenols,
the 2,6-dinaphthylphenols,
2,6-dimethoxyphenol,
2,6-diethoxyphenol,
2,6-diphenoxyphenol,
2-methyl-6-tert-butylphenol,
the 2-propyl-6-phenylphenols, etc.

The $R^1$ and $R^2$ substituents of Formula I. can be the same or different and can be selected from the group consisting of alkyl, cycloalkyl, aryl, alkoxy, cycloalkoxy, aryloxy, and combinations thereof. A preferred phenol reactant class within the practice of this invention are the phenols having 2,6-substituents selected from the lower alkyl group consisting of $C_{1-2}$ radicals. Particularly preferred is 2,6-dimethylphenol, also known as 2,6-xylenol.

My process employs sulfur in any of its elemental forms or as polysulfide ions represented by the generic formula $M_yS_x$ wherein $x$ is a positive integer at least equal to 2 and wherein M is selected from the group consisting of alkali and alkaline earth metals as well as ammonium ions $R_4N^+$ where R is hydrogen or a hydrocarbon. Preferably elemental sulfur is employed. Because of its economic advantage, elemental sulfur can be employed in any of the commonly known commercial forms, such as bright sulfur (99.5%), dark sulfur (up to 1% carbonaceous material) refined sulfur (99.8%); high purity sulfur (99.97%); sublimed sulfur (flowers of sulfur); flour sulfur, ground refined or crude sulfur in various mesh sizes; and Rubbermakers, a ground special grade.

Any base that can be employed which will dissolve in the phenol reaction mixture and form a phenoxide ion (sometimes referred to as a metal phenolate)representative among others, of basic species which can be employed are elemental alkali and alkaline earth metals; ammonium, alkali or alkaline earth metal hydroxides; salts of strong bases and weak organic acids; etc. Specific examples of the aforementioned are sodium, potassium, magnesium metal; ammonium, sodium, potassium, lithium, and calcium hydroxide; ammonium, sodium, lithium, and barium carbonates, sodium acetate, sodium benzoate, sodium methylate, sodium thiosulfate, sodium sulfide, sodium tetrasulfide, sodium cyanide, etc. Preferred basic species are the metals sodium and potassium, sodium and potassium hydroxides and salts of sodium and potassium bases and weak organic acids.

In accordance with the process of this invention, in addition to the phenol, sulfur and base, the process is carried out in the presence of a promoter which shifts the equilibrium point of the reaction in favor of the formation of the thiobisphenol. These promoters are selected from the class consisting of activated olefins and epoxy compounds. Among others, activated olefin compounds may be represented by the Formula II set out hereafter;

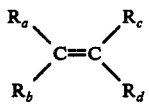
II.

wherein independently at least one of the $R_a$, $R_b$, $R_c$ and $R_d$ substituents is selected from the electron-attracting group consisting of cyano, i.e. —CN; carbomoyl, i.e. —CON(R')$_2$; oxycarbonyl, i.e. —COOR''; oxohydrocarbyl, i.e., —COR''; wherein independently each R' represents hydrogen, acyclic and cyclic hydrocarbon radicals, independently R'' represents acyclic and cyclic hydrocarbon radicals.

Preferably the activated olefins have from 3 to 10 carbon atoms, more preferably from 3 to 5 carbon atoms. The olefins may be either mono- or polyolefinic and may be either conjugated or nonconjugated in unsaturation. Among others, representative of activated olefin species are such compounds as acrylamide, α-methylacrylamide, N-methylacrylamide, N-phenylacrylamide, N,N-diisobutylacrylamide, acrylonitrile, α-phenylacrylonitrile, vinyl chloride, vinylidene chloride, vinyl methyl ether, vinyl ethyl ether, vinyl n-propyl ether, vinyl n-octyl ether, vinyl n-octadecyl ether, vinylidenecyanide, sometimes referred to as methylene malonitrile, vinyl succinimide, N-vinyl N-methylacetamide, N-vinyl N-phenylacetamide, N-vinyl diglycolylimide, etc. Preferred olefins are monoolefinic C$_3$–C$_5$ carbonitrides, such as acrylonitrile, α-methyl acrylonitrile, α-ethyl acrylonitrile, butyronitrile and α-methylbutyronitrile.

Among others, epoxy compounds can be represented by the Formula III set out hereafter:

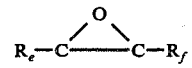
III.

wherein independently each $R_e$ and $R_f$ substituents are selected from the group consisting of hydrogen, acyclic and cyclic radicals. Preferably, the $R_e$ and $R_f$ radicals are free of any electron-attracting substituents which can substantially reduce the ease of carbon-oxygen bond breakage. Preferred epoxy compounds are epoxides containing from 2 to 10 carbon atoms, more preferably from 2 to 5 carbon atoms. The epoxides may be mono- or polyepoxy compounds, i.e. compounds which contain more than one reactive epoxy group. Among others, representative of epoxy compounds are such compounds as ethylene oxide, propylene oxide, 1,2-butyleneoxide, also known as 1,2-epoxybutane, trimethylethylene oxide, tetramethylethylene oxide, butadiene monoxide, styrene oxide, α-methylstyrene oxide, 1,1-diphenylethylene oxide, hexyl glycidyl ether, allyl glycidyl ether, phenyl glycidyl ether, o-chlorophenyl glycidyl ether, methacrylyl chloride epoxide, glycidyl methacrylate, 1,2-epoxy-4-vinylcyclohexane, 2,3-epoxyoctane, 4-butylphenyl glycidyl ether, dipentene monoxide, α-pinene oxide, etc. Preferred epoxides are C$_2$–C$_5$ monoepoxides, such as ethyleneoxide, propyleneoxide, 1,2-butyleneoxide and trimethylethyleneoxide.

In general, the process can be carried out in the absence of any solvent, e.g. where the phenol acts as both a reactant and as a solvent, or in the presence of any solvent which forms a solution in combination with phenol, sulfur, base and the promoter. As illustrated both by description of this process as well as the process for the preparation of the organomercaptophenols described in my copending application Ser. No. 484,996, now U.S. Pat. No. 3,979,460, filed concurrently herewith, assigned to the same assignee as this invention, the type of solvent employed in the reaction media is critical. In general, in the process of this invention, it is desirable when thiobisphenols are desired as the optimum resulting reaction product, in contradistinction to the process described in our aforementioned copending application when organomercaptophenols are desired as the optimum resulting reaction product, that the solvent employed be selected from a group consisting of any nonpolar or polar solvent subject to the proviso that the solvent employed be substantially free of high dielectric constant solvents, i.e. solvents incapable of strong hydrogen bonding to the phenol reactant or any intermediates derived therefrom during the course of the reaction. In general, the solvents which are excluded are solvents commonly referred to as dipolar aprotic solvents which solvents are characterized as solvent species which do not have the capability of donating strong hydrogen bonding to solute species and which have high dielectric constants, e.g. dielectric constants of from about 20 to about 50, or higher. Among others, suitable solvents in the process of this invention that can be employed are essentially:

(A) non- or lowpolar solvents such as hexane, 3-methylpentane, heptane, cyclohexane, methylcyclohexane, cyclohexane, isooctane, p-cymene, cumene, lowpolar decalin, toluene, benzene, diethylether, diphenylether, dioxane, thiophene, dimethysulfide, ethyl acetate, tetrahydroduran, etc., and mixtures thereof; and (B) mediumpolar solvents such as chlorobenzene, anisol, bromobenzene, t-butanol, ethanol, methanol, o-dichlorobenzene, methyl formate, iodobenzene, acetone, acetophenone, etc. and mixtures thereof. Specifically excluded from this process are substantial amounts of any polar solvent having high dielectric constants such as N-methylformamide, N,N-dimethylformamide, acetonitrile, nitrobenzene, γ-butyrolactone, nitromethane, dimethylsulfoxide, sulpholane and N-methylpyrrolidone, etc. and mixtures thereof. In a preferred embodiment of this invention, it is preferred that the reaction be carried out in the presence of a lowpolar solvent as defined hereinbefore which is characterized in accordance with solvent polarity scales described in the publication *Solute-Solvent Interactions*, J. F. Kotese and K. D. Richey (1969) Marcel Dekker, pages 281–282.

Although not wishing the process of this invention or the scope thereof to be limited by any theory, it is believed that both the rate constants and equilibrium constants associated with the process of this invention are related to (1) the promoter employed, and wherein a solvent other than phenol is employed, to (2) the polarity and the dielectric strength of the solvent employed in the preparation of thiobisphenols. It is also believed that a proton-transfer reaction is involved which transfer rate and equilibrium constant is significantly affected by the solvent both in its initial and transition state. It is further postulated that wherein a non-, low- or medium-polar solvent is employed, thiobisphenols rather than organomercaptophenols are the major reaction product because of the ability of the non-, low- or mediumpolar solvents to form strong hydrogen bonds which substantially affect chemical behavior of an intermediate species formed within the reaction media in the presence of the phenol, sulfur, base and promoter.

In general, as stated hereinbefore, the process of this invention can be carried out under reaction parameters which broadly comprise contacting a 2,6-disubstituted phenol with sulfur in the presence of a base and a promoter. The reaction, I believe, proceeds principally according to the following equation:

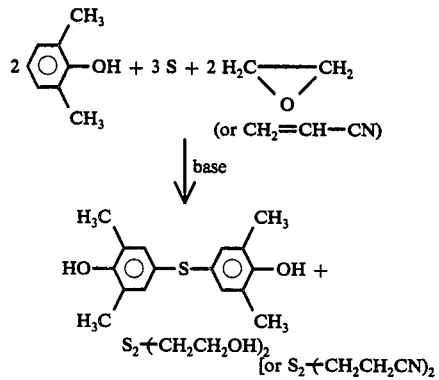

It is important that the epoxide or activated olefin be added slowly during the course of the reaction, otherwise a side reaction occurs as shown in the following equation:

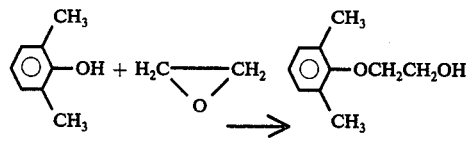

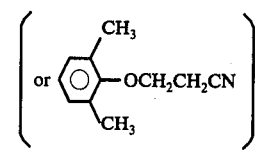

When the initial reaction to form the monothiobisphenol(II) is finished, the addition of further epoxide or activated olefin promoter to the reaction mixture results in the formation of products resulting from the reaction of the epoxide or activated olefin with the phenolic hydroxy group, e.g. X and XI,

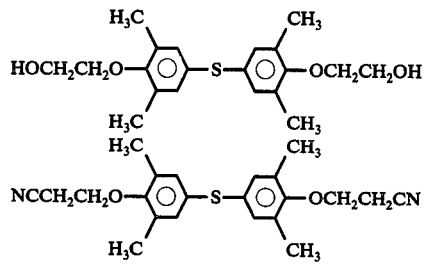

The phenol: sulfur mole ratio can vary widely, however, because approximately 3 gram atom of sulfur reacts with 2 moles of phenol and 2 moles of promoter in the preparation of a thiobisphenol or with 4 moles of the promoter if the desired product is the thiobisphenol adduct, a minimum mole:gram atom ratio preferably employed in my process is 1 mole of phenol to 1.5 gram atom of sulfur. The reaction can be carried out at any phenol:sulfur ratio such as ratios within the range of from about 1:0.05 to about 1:20, however, preferably ratios within the range of from about 1:0.5 to about 1:5 and more preferably from about 1:1 to about 1:2 are employed. Any mole ratio of phenol to base can be employed and can be varied widely. In general, suitable ratios include the use of base in catalytic amounts, e.g. wherein the phenol:base mole ratios are as low as 1:0.001 (0.1 mole % base based on phenol) as well as noncatalytic amounts, e.g. wherein the phenol:base mole ratios are as high as 1:2 (200 mole % base based on phenol) or even higher. In general, satisfactory phenol:base proportions are within the range of from about 1:0.01 to about 1:1, more preferably from about 1:0.02 to about 5:1 and even more preferably from about 1:0.05 to about 1:0.10.

The amount of promoter which is employed can be varied over a wide range. In general, suitable phenol to promoter mole ratio are within the range of from about 1:0.1 to about 1:10, more preferably from about 1:0.2 to about 1:5 and even more preferably from about 1:0.5 to about 1:2.5. In order to reduce the opportunity of olefin or epoxy addition to the resulting thiobisphenols reaction products preferably the phenol:promoter mole proportions are reconstructed to mole ratios no greater than about 1:1 and preferably less than from about 1:0.5 to about 1:1.5. In a preferred embodiment, it is preferred that the promoter be added to the reaction medium in a programmed manner, i.e. in a manner in which continuously regulates the amount of promoter admitted to the reaction medium in order to insure that the equilibrium and rate constants of the reaction favored in the formation of the thiobisphenols rather than the formation of thiobisphenols further reacted with the olefin or epoxy compound.

In general, any reaction temperature can be employed wherein the thermal reaction kinetics are not deleterious to reaction rates, reaction time, yield and/or conversion of the phenol to the desired thiobisphenol. In general, the reaction temperatures can be varied widely, however, they often fall within the range of from about 0° C. to about 200° C., and more often fall within the temperature range of from about 80° C. to about 120° C. particularly. The reaction periods also vary widely, however, generally falling within the range of from about ½ hour to about 5 hours. The process is preferentially carried out in the presence of an inert atmosphere of nitrogen in order to exclude from the reaction medium any oxygen or oxidizing agents which are well-known to oxidize organic sulfides to sulfoxides or sulfones among other undesirable reaction products.

The amount of solvent when employed in accordance with a preferred embodiment of this invention can be employed in any amount and can vary widely. In general, the solvent to phenol ratio which is generally suited to the process of this invention can be within the range of from about 1000:1 to about 1:1 preferably from about 100:1 to about 2:1 and even more preferably from about 10:1 to about 5:1. As indicated hereinbefore, in view of the effect of the solvent employed on the major end product, i.e., thiobisphenols, obtained by the practice of this invention, as opposed to the major end product, i.e. organomercaptophenols, obtained by the practice of my copending invention described in my copending application referred to hereinbefore, Ser. No. 484,996, now U.S. Pat. No. 3,979,460, those skilled in the art will readily be able to determine by means of simple experimentation any economic benefits which may be derived from solvent mixtures which include both non-, low- or mediumpolar and high dielectric polar solvents.

By the practice of this invention, as described hereinbefore, thiobis-2,6-disubstituted phenols and O-alkylated thiobis-2,6-disubstituted phenols can be prepared having the following structural formula:

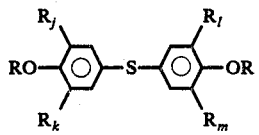

XII.

wherein independently each $R_j$, $R_k$, $R_l$, and $R_m$ is a monovalent substituent selected from the group consisting of hydrocarbon and hydrocarbonoxy radicals, and each R is selected from the group consisting of hydrogen and cyano, carbamoyl, oxycarbonyl, oxyhydrocarbyl, hydroxy substituted monovalent acyclic and cyclic hydrocarbon radicals.

Preferably, the radicals $R_j$, $R_k$, $R_l$ and $R_m$ contain from 1 to 30, more preferably from 1 to 15, and even more preferably from 1 to 2 carbon atoms, and R contains from 2 to 30, more preferably from 2 to 15, and even more preferably from 2 to 6 carbon atoms. The hydrocarbon and hydrocarbonoxy substituents of XII, can be the same or different and can be selected from the group consisting of alkyl, cycloalkyl, aryl, alkoxy, cycloalkoxy, aryloxy and combinations thereof.

In order that those skilled in the art may better understand my invention, the following examples are given which are illustrative of the best mode of this invention, however, these examples are not intended to limit the invention in any manner whatsoever. In all of the examples, all parts are by weight unless otherwise stated and the following general procedure was employed. For purposes of brevity, only deviations from this procedure will be set out in the examples.

General Procedure

A solution of phenol, e.g. 2,6-dimethylphenol, and a solvent when employed, e.g. xylene, is charged to a reaction vessel. Base, sodium metal, is added to the phenol solvent mixture and heated to elevated temperatures, e.g. about 100° C. until dissolved. The mixture is cooled, e.g. to a temperature of about 70°–80° C., and sulfur, e.g. elemental sulfur (flowers of sulfur), is added to the reaction mixture. The mixture is heated to elevated temperatures, e.g. temperatures about 100° C., and the promoter is added over a 2–4 hour period. The resulting reaction mixture, generally, is not homogeneous and vigorous stirring is required. The mixture is cooled and diluted if necessary with a suitable diluent, e.g. ether, and washed with dilute hydrochloric acid and then with water and dried with a suitable drying agent, e.g. $MgSO_4$. The resulting product after removal of the solvent is purified by distillation or by recrystallization from a suitable solvent, e.g. acetic acid. The thiobisphenol recovered is characterized by its melting point in both its crude and purified form, and analytically characterized, based upon a correlation between calculated and found carbon, hydrogen, oxygen, sulfur of thiobisphenol.

If the product desired is the bis adduct of the thiobisphenol with two moles of promoter, the reaction mixture after cooling and dilution with a suitable solvent, e.g. ether, is washed with dilute sodium hydroxide to separate any phenolic materials and the residue after drying and removing solvent is distilled to yield pure product.

TABLE I

Summary of Experimental Data - Run Nos. 1–23

| Run No. | Reaction Products Composition | Yield | Reactants(R), Base(B), Solvent(S), Promoter(P) | | Conv. | Temp. | Time | Mole Ratios Phenol:Sulfur:Base:Promoter |
|---|---|---|---|---|---|---|---|---|
| 1. | (a) 4,4'-dihydroxy-3,3',5,5'-tetraphenyldiphenyl sulfide, Analysis:calc.:82.73C,5.01H,6.13S found:82.4C,4.98H,5.9S | 32% | (R) 2,6-diphenylphenol, sulfur, (B) sodium hydroxide, (S) xylene, (P) — | 246g(1.0m) 32g(1.0m) 40g(1.0m) 1230ml | 32% | 169° C | 2 hrs | 1:1:1:0 |
|  | (b) 4,4'-dihydroxy-3,3',5,5'-tetraphenyldiphenyl disulfide | trace est.≈1% |  |  |  |  |  |  |
| 2. | (a) 4,4'-dihydroxy-3,3',5,5'-tetramethyldiphenyl sulfide | 86%, (94.7g) | (R) 2,6-xylenol, sulfur, (B) sodium metal, | 122.2g(1.0m) 48 g(1.5m) 2.3g(0.1m) | 80% | 80° C | 4.25 hrs | 1:1.5:0.1:1 |
|  | (b) β,β'-dithiobispropionitrile | 9%, (12.1g) | (S)— |  |  |  |  |  |

TABLE I-continued

Summary of Experimental Data - Run Nos. 1-23

| Run No. | Reaction Products Composition | Yield | Reactants(R), Base(B), Solvent(S), Promoter(P) | | Conv. | Temp. | Time | Mole Ratios Phenol:Sulfur:Base:Promoter |
|---|---|---|---|---|---|---|---|---|
| 3. | (a) 4,4'-dihydroxy-3,3',5,5'-tetraphenyldiphenyl sulfide, Analysis:calc.:82.73C,5.01H,6.13S found:82.4C,4.98H,5.9S | 87%, (100g) (S) — | (P) acrylonitrile, (R) 2,6-xylenol, sulfur, (B) sodium metal, | 53.1g(1.0m) 122g(1.0m) 48g(1.5m) 1.2g(0.05m) | 85% | 100° C | 4 hrs | 1:1.5:0.05:1 |
| | (b) 2,6-dimethylphenoxypropanol-2 | 11.6%, (20.9g) | (P) propylene oxide | 58.1g(1.0m) | | | | |
| 4. | (a) 4,4'-dihydroxy-3,3',5,5'-tetraphenyldiphenyl sulfide, Analysis:calc.:82.73C,5.01H,6.13S found:82.4C,4.98H,5.9S | 5% (S) — | (R) 2,6-xylenol, sulfur, (B) sodium metal, | 29.3g(0.24m) 6.4g(0.2m) 0.23g(0.01m) | 25% | 50° C | 24 hrs | 1:1:0.05:1.75 |
| | (b) 2,6-dimethylphenoxypropanol-2 | 25% | (P) propylene oxide, | 20.3g(0.35m) | | | | |
| 5. | (a) 4,4'-dihydroxy-3,3',5,5'-tetra-t-butyldiphenyl sulfide, (b) 4,4'-dihydroxy-3,3',5,5'-tetra-t-butylbiphenyl | 25% 7% | (R) 2,6-di-t-butylphenol sulfur, (B) sodium metal, (S) — | 206g(1.0m) 48g(1.5m) 1.2g(0.05m) | 38% | 110° C | 2 hrs | 1:1.5:0.05:1 |
| 6. | (a) 4,4'-(2-hydroxypropoxy)-3,3',5,5'-tetramethyldiphenyl sulfide Analysis:calc.:67.67C,7.74H,8.20S found:67.40C,7.98H,8.3S | 76%, (133g) | (P) propylene oxide, (R) 2,6-xylenol, sulfur, (B) sodium metal, (S) — | 58.1g(1.0m) 122g(1.0m) 48g(1.5m) 1.2g(0.05m) | 89% | 100° C | 2 hrs | 1:1.5:0.05:1 |
| | (b) 2,6-dimethylphenoxypropanol-2 | 16%, (28.8g) | (P) propylene oxide | 174.3g(3.0m) | | | | |
| 7. | (a) 4,4'-dihydroxy-3,3',5,5'-tetramethyldiphenyl sulfide (b) 2,6-dimethylphenoxypropanol-2 | 38% 17% | (R) 2,6-xylenol, sulfur, (B) sodium metal, (S) — | 122.2g(1.0m) 48g(1.5m) 2.3g(0.1m) | 80% | 80° C | 2 hrs | 1:1.5:0.1:1 |
| 8. | (a) 4,4'-dihydroxy-3,3',5,5'-tetramethyldiphenyl sulfide | 32%, (50.0g) | (P) propylene oxide, (R) 2,6-xylenol, sulfur, (B) sodium metal, (S) — | 58.1g(1.0m) 122.2g(1.0m) 48g(1.5m) 1.2g(0.05m) | 87% | 110° C | 5 hrs | 1:1.5:1.0:0.05 |
| 9. | (a) 4,4'-dihydroxy-3,3',5,5'-tetramethyldiphenyl sulfide (b) 2,6-dimethylphenoxypropanol-2 | 24% 4% | (P) propylene oxide, (R) 2,6-xylenol, sulfur, (B) sodium metal, (S) — | 58.1g(1.0m) 122.2g(1.0m) 48g(1.5m) 1.2g(0.05m) | 75% | 120° C | 4 hrs | 1:1.5:0.05:1 |
| 10. | (a) 2,6-dimethylphenoxypropanol-2 (b) 4,4'-dihydroxy-3,3',5,5'-tetramethyldiphenyl sulfide | 55% 47% | (P) propylene oxide, (R) 2,6-xylenol, sulfur, (B) sodium hydroxide, (S) benzene,nm | 58.1g(1.0m) 12.2g(0.1m) 3.2g(0.1m) 0.4g(0.01m) 50ml | 20% | 80° C | 6 hrs | 1:1:0.01:1 |
| 11. | (a) 2,6-dimethylphenoxypropanol-2 (b) 4,4'-dihydroxy-3,3',5,5'-tetramethyldiphenyl sulfide | 41% 5% | (P) propylene oxide, (R) 2,6-xylenol, sulfur, (B) sodium hydroxide, (S) ethylene glycol, (P) propylene oxide | 6.4g(0.11m) 12.2g(0.1m) 3.2g(0.1m) 0.4g(0.01m) 62ml 6.4g(0.11m) | 98% | 80° C | 6 hrs | 1:1:0.01:1 |
| 12. | (a) 4,4'-(2-hydroxyethoxy)-3,3',5,5'-tetramethyldiphenyl sulfide Analysis:calc.:66.28C,7.23H,8.83S found:66.4C,7.2H,8.9S | 67% | (R) 2,6-xylenol, sulfur, (B) sodium metal, (S) — | 122.2g(1.0m) 48g(1.5m) 1.2g(0.05m) | 100% | 100° C | 5 hrs | 1:1.5:0.05:excess |
| | (b) 2,6-dimethylphenoxyethanol | 12% | (P) ethylene oxide, | in excess g | | | | |
| 13. | (a) 4-cyanothioethoxy-2,6-dimethylphenol Analysis:calc.:63.75C,6.32H, 6.76N15.44S found:63.2C,6.3H,6.8N,15.3S | 34%, (24.2g) | (R) 2,6-xylenol, sulfur, (B) sodium hydroxide, (S) N-methylpyrrolidone, toluene, (P) sodium hydroxide, | 61.0g(0.5m) 32.1g(1.0m) 20.0g(0.5m) 310ml 60ml 20.0g(0.5m) | 69% | 120° C | 4 hrs | 0.5:1.0:0.5:1.5 |
| | (b) 4,4'-dihydroxy-3,3',5,5'-tetramethyldiphenyl sulfide | est.≃1% | | | | | | |
| 14. | (a) 4,4'-dihydroxy-3,3',5,5'-tetramethyldiphenyl sulfide (b) β,β'dithiobispropionitrile (c) 2-(2,6-dimethylphenoxy)-propionitrile | 34%, (9.2g) 41%, (7.3g) 21%, (3.6g) | (R) 2,6-xylenol, sulfur, (B) metallic sodium, (S) — (P) acrylonitrile, | 14.66g(0.12m) 6.4g(0.2m) 0.23g(0.01m) 15.9g(0.3m) | 98% | 50° C | 9 hrs | 1:2:0.1:13 |
| 15. | (a) 4,4'-dihydroxy-3,3',5,5'-tetramethyldiphenyl sulfide (b) 3-(2,6-dimethylphenoxy)propionitrile | 50% 37% | (R) 2,6-xylenol, sulfur, (B) sodium metal, (S) — (P) acrylonitrile | 12.2g(0.1m) 3.2g(0.1m) 0.12g(.005m) 5.3g(0.1m) | 50% | 50° C | 24 hrs | 1:1:0.05:1 |
| 16. | (a) 4,4'-dihydroxy-3,3',5,5'-tetramethyldiphenyl sulfide (b) 3-(2,6-dimethylphenoxy)propio- | 50% 37% | (R) 2,6-xylenol, sulfur (B) metallic sodium, | 14.7g(0.12m) 3.2g(0.1m) 0.46g(0.02m) | 50% | 50° C | 24 hrs | 1:1:.2:1 |

TABLE I-continued
Summary of Experimental Data - Run Nos. 1-23

| Run No. | Reaction Products Composition | Yield | Reactants(R), Base(B), Solvent(S), Promoter(P) | | Conv. | Temp. | Time | Mole Ratios Phenol: Sulfur: Base: Promoter |
|---|---|---|---|---|---|---|---|---|
| | nitrile | | (S) —  (P) acrylonitrile | 5.3g(0.1m) | | | | |
| 17. | (a) 4,4'-dihydroxy-3,3',5,5'-tetra-methyldiphenyl sulfide | 39% | (R) 2,6-xylenol, sulfur, (B) aqueous NaOH, (S) benzene, (P) acrylonitrile, | 14.6g(0.12m) 3.2g(0.1m) 4.0g(0.1m) 10ml 5.3g(0.1m) | 56% | 50° C | 24 hrs | 1:1:1:1 |
| 18. | (a) 4,4'-dihydroxy-3,3',5,5'-tetra-methyldiphenyl sulfide (b) 4,4'-(2-cyanoethoxy)-3,3',5,5'-tetramethyldiphenyl sulfide (c) β,β'-dithiobispropionitrile, | 41% 36% 3% trace | (R) 2,6-xylenol, sulfur (B) KOH (aqueous), (S) — (P) acrylonitrile, | 14.7g(0.12m) 3.2g(0.1m) 0.56g(0.01m) 5.3g(0.1m) | 59% | 50° C | 24 hrs | 1:1:.1:1 |
| 19. | (a) 4,4'-dihydroxy-3,3',5,5'-tetra-methylphenyl sulfide | 0% | (R) 2,6-xylenol, sulfur, (B) Al(aluminum foil), (S) — (P) acrylonitrile | 12.2g(0.1m) 3.2g(0.1m) 0.08g(0.003m) 10.6g(0.2m) | | 50° C | 1 hr | 1:1:0.03:2 |
| 20. | (a) 4,4'-dihydroxy-3,3',5,5'-tetra-methyldiphenyl sulfide | 0% | (R) 2,6-xylenol, sulfur, (B) Al(aluminum foil), (S) — (P) acrylonitrile, | 12.2g(0.1m) 3.2g(0.1m) 0.08g(0.003m) 10.6g(0.2m) | | 80° C | 1 hr | 1:1:0.03:1 |
| 21. | (a) 4,4'-dihydroxy-3,3',5,5'-tetra-methyldiphenyl sulfide (b) β,β'-dithiobispropionitrile | est.≈1% trace <1% | (R) 2,6-xylenol, sulfur, (B) Al(aluminum foil), (S) — (P) acrylonitrile, | 12.2g(0.1m) 3.2g(0.1m) 0.08g(0.003m) 10.6g(0.2m) | | 90° C | 24 hrs | 1:1:0.03:1 |
| 22. | (a) 4,4'-dihydroxy-3,3',5,'-tetra-methyldiphenyl sulfide (b) β,β'-dithiobispropionitrile | 20% 1% | (R) 2,6-xylenol, sulfur, (B) lithium metal, (S) — (P) acrylonitrile, | 12.2g(0.1m) 3.2g(0.1m) 0.07g(0.01m) 11.6g(0.2m) | 50% | 80° C | 24 hrs | 1:1:0.1:2 |
| 23. | (a) 4,4'-dihydroxy-3,3',5,5'-tetra-methyldiphenyl sulfide (b) 3-(2,6-dimethylphenoxy)-2-methylpropionitrile | 26% 22% | (R) 2,6-xylenol, sulfur (B) sodium metal, (S) — (P) methacrylonitrile, | 12.2g(0.1m) 3.2g(0.1m) 0.23g(0.01m) 13.4g(0.2m) | 40% | 80° C | 24 hrs | 1:1:0.1:2 |

Thiobisphenols produced by this process are useful as monomers in the synthesis of polyesters, polycarbonates, polyethers, epoxy resins, among many other chemicals synthesized from polyhydric phenols. In addition, the thiobisphenols are also useful as antioxidants.

Several modifications and variations of the invention have been illustrated in the above examples and elsewhere in the disclosure. Accordingly, other modifications and variations will be readily apparent to those skilled in the art in view of applicant's teaching. It is, therefore, to be understood that changes may be made in the particular embodiments of the invention described herein which changes are within the full intended scope of the invention as defined by the appended claims.

What I claim as new and desire to secure by Letters Patent in the United States is:

1. A thiobisphenol of the formula:

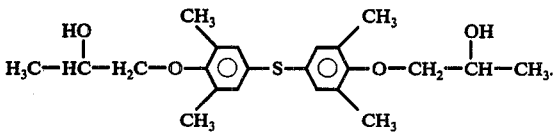

2. A thiobisphenol of the formula:

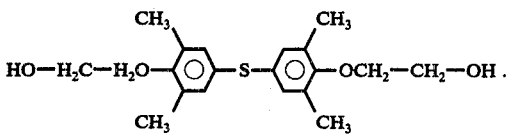

* * * * *